United States Patent
Rinner et al.

(10) Patent No.: US 9,005,249 B2
(45) Date of Patent: Apr. 14, 2015

(54) SPINAL ROD CONNECTOR ASSEMBLY

(75) Inventors: James A. Rinner, Franksville, WI (US);
Michael S. Butler, St. Charles, IL (US);
Seetal K. Erramilli, Naperville, IL (US)

(73) Assignee: Life Spine, Inc., Huntley, IL (US)

( * ) Notice: Subject to any disclaimer, the term of this patent is extended or adjusted under 35 U.S.C. 154(b) by 197 days.

(21) Appl. No.: 13/546,588

(22) Filed: Jul. 11, 2012

(65) Prior Publication Data
US 2013/0018422 A1 Jan. 17, 2013

Related U.S. Application Data

(60) Provisional application No. 61/506,373, filed on Jul. 11, 2011.

(51) Int. Cl.
*A61B 17/70* (2006.01)

(52) U.S. Cl.
CPC ......... *A61B 17/7049* (2013.01); *A61B 17/7041* (2013.01)

(58) Field of Classification Search
USPC .................................................. 606/250–278
See application file for complete search history.

(56) References Cited

U.S. PATENT DOCUMENTS

| | | |
|---|---|---|
| 2,414,882 A | 1/1947 | Longfellow |
| 3,289,290 A | 12/1966 | Sandor |
| 4,399,814 A | 8/1983 | Pratt et al. |
| 4,648,388 A | 3/1987 | Steffee |
| 4,653,489 A | 3/1987 | Tronzo |
| 4,790,297 A | 12/1988 | Luque |
| 4,805,602 A | 2/1989 | Puno et al. |
| 4,863,472 A | 9/1989 | Tormala et al. |
| 5,047,029 A | 9/1991 | Aebi et al. |
| 5,092,893 A | 3/1992 | Smith |
| 5,098,435 A | 3/1992 | Stednitz et al. |
| 5,129,899 A | 7/1992 | Small et al. |
| 5,190,543 A | 3/1993 | Schlapfer |
| 5,261,909 A | 11/1993 | Sutterlin et al. |
| 5,350,380 A | 9/1994 | Goble et al. |
| 5,352,226 A | 10/1994 | Lin |
| 5,423,819 A | 6/1995 | Small et al. |

(Continued)

FOREIGN PATENT DOCUMENTS

| | | |
|---|---|---|
| DE | 92 15 561 | 1/1993 |
| WO | WO-02/36026 A2 | 5/2002 |

(Continued)

OTHER PUBLICATIONS

"The Trio® Spinal System," printed Feb. 9, 2005, 2 pages.

(Continued)

*Primary Examiner* — Jan Christopher Merene
(74) *Attorney, Agent, or Firm* — Foley & Lardner LLP

(57) ABSTRACT

A spinal rod connector assembly for use with a vertebral bone screw has an articulating clamp for 1) fixing an orientation of the spinal rod connector assembly relative to and on the vertebral bone screw, and 2) attaching a separate spinal rod onto the spinal rod connector assembly in concert with one another. The articulating clamp resides in a body of the spinal rod connector assembly and transfers a received downward force laterally to a spinal rod component of the spinal rod connector assembly which is configured to abut the spinal rod and hold the spinal rod between itself and a spinal rod holder of the spinal rod connector assembly. The articulating clamp thus improves the force transfer efficacy of the system.

20 Claims, 2 Drawing Sheets

(56) References Cited

U.S. PATENT DOCUMENTS

| | | |
|---|---|---|
| 5,449,257 A | 9/1995 | Giannuzzi |
| 5,501,684 A | 3/1996 | Schlapfer et al. |
| 5,545,163 A | 8/1996 | Miller et al. |
| 5,562,661 A | 10/1996 | Yoshimi et al. |
| 5,569,252 A | 10/1996 | Justin et al. |
| 5,582,612 A | 12/1996 | Lin |
| 5,584,833 A | 12/1996 | Fournet-Fayard et al. |
| 5,611,800 A | 3/1997 | Davis et al. |
| 5,613,968 A | 3/1997 | Lin |
| 5,643,262 A | 7/1997 | Metz-Stavenhagen et al. |
| 5,643,263 A | 7/1997 | Simonson |
| 5,645,547 A | 7/1997 | Coleman |
| 5,649,931 A | 7/1997 | Bryant et al. |
| 5,667,513 A | 9/1997 | Torrie et al. |
| 5,688,272 A | 11/1997 | Montague et al. |
| 5,688,275 A | 11/1997 | Koros et al. |
| 5,855,285 A | 1/1999 | Laird et al. |
| 5,885,285 A | 3/1999 | Simonson |
| 5,938,663 A | 8/1999 | Petreto |
| 5,941,885 A | 8/1999 | Jackson |
| 5,947,967 A | 9/1999 | Barker |
| 5,976,135 A | 11/1999 | Sherman et al. |
| 6,001,098 A | 12/1999 | Metz-Stavenhagen et al. |
| 6,030,388 A | 2/2000 | Yoshimi et al. |
| 6,033,406 A | 3/2000 | Mathews |
| 6,045,555 A | 4/2000 | Smith et al. |
| 6,048,343 A | 4/2000 | Mathis et al. |
| 6,059,785 A | 5/2000 | Schavan et al. |
| 6,063,089 A | 5/2000 | Errico et al. |
| 6,063,090 A | 5/2000 | Schlapfer |
| 6,086,588 A | 7/2000 | Ameil et al. |
| 6,096,060 A | 8/2000 | Fitts et al. |
| 6,111,164 A | 8/2000 | Rainey et al. |
| 6,123,706 A | 9/2000 | Lange |
| 6,139,549 A | 10/2000 | Keller |
| 6,146,383 A | 11/2000 | Studer et al. |
| 6,159,210 A | 12/2000 | Voor |
| 6,179,838 B1 | 1/2001 | Fiz |
| 6,183,473 B1 | 2/2001 | Ashman |
| 6,187,005 B1 | 2/2001 | Brace et al. |
| 6,210,376 B1 | 4/2001 | Grayson |
| 6,210,413 B1 | 4/2001 | Justis et al. |
| 6,231,575 B1 | 5/2001 | Krag |
| 6,248,104 B1 | 6/2001 | Chopin et al. |
| 6,248,107 B1 | 6/2001 | Foley et al. |
| 6,254,602 B1 | 7/2001 | Justis |
| 6,315,779 B1 | 11/2001 | Morrison et al. |
| 6,317,957 B1 | 11/2001 | Gregor et al. |
| 6,355,039 B1 | 3/2002 | Troussel et al. |
| 6,371,957 B1 | 4/2002 | Amrein et al. |
| 6,379,357 B1 | 4/2002 | Bernstein et al. |
| 6,402,749 B1 | 6/2002 | Ashman |
| 6,471,703 B1 | 10/2002 | Ashman |
| 6,482,207 B1 | 11/2002 | Errico |
| 6,520,962 B1 | 2/2003 | Taylor et al. |
| 6,582,436 B2 | 6/2003 | Schlapfer et al. |
| 6,613,050 B1 | 9/2003 | Wagner et al. |
| 6,616,665 B2 | 9/2003 | Grafton et al. |
| 6,626,906 B1 | 9/2003 | Young |
| 6,641,583 B2 | 11/2003 | Shluzas et al. |
| 6,641,586 B2 | 11/2003 | Varieur |
| 6,648,887 B2 | 11/2003 | Ashman |
| 6,648,894 B2 | 11/2003 | Abdelgany et al. |
| 6,663,642 B2 | 12/2003 | Beyar et al. |
| 6,668,688 B2 | 12/2003 | Zhao et al. |
| 6,676,661 B1 | 1/2004 | Benlloch et al. |
| 6,685,705 B1 | 2/2004 | Taylor |
| 6,706,045 B2 | 3/2004 | Lin et al. |
| 6,723,100 B2 | 4/2004 | Biedermann et al. |
| 6,755,835 B2 | 6/2004 | Schultheiss et al. |
| 6,786,907 B2 | 9/2004 | Lange |
| 6,827,722 B1 | 12/2004 | Schoenefeld |
| 6,832,999 B2 | 12/2004 | Ueyama et al. |
| 6,835,196 B2 | 12/2004 | Biedermann et al. |
| 6,858,030 B2 | 2/2005 | Martin et al. |
| 6,887,242 B2 | 5/2005 | Doubler et al. |
| 6,893,444 B2 | 5/2005 | Orbay |
| 6,899,714 B2 | 5/2005 | Vaughan |
| 6,945,972 B2 | 9/2005 | Frigg et al. |
| 6,947,967 B2 | 9/2005 | Ferris et al. |
| 6,949,100 B1 | 9/2005 | Venturini |
| 6,951,561 B2 | 10/2005 | Warren et al. |
| 7,022,122 B2 | 4/2006 | Amrein et al. |
| 7,163,539 B2* | 1/2007 | Abdelgany et al. ......... 606/86 A |
| 7,261,715 B2* | 8/2007 | Rezach et al. ................. 606/60 |
| 7,575,587 B2 | 8/2009 | Rezach et al. |
| 7,594,924 B2 | 9/2009 | Albert et al. |
| 7,604,643 B2 | 10/2009 | Ciccone et al. |
| 7,678,137 B2 | 3/2010 | Butler et al. |
| 7,744,632 B2 | 6/2010 | Usher |
| 7,744,635 B2 | 6/2010 | Sweeney et al. |
| 7,938,848 B2 | 5/2011 | Sweeney |
| 8,021,398 B2 | 9/2011 | Sweeney et al. |
| 8,066,746 B2 | 11/2011 | Glerum et al. |
| 8,070,781 B2 | 12/2011 | Harper |
| 8,221,473 B2* | 7/2012 | Butler et al. ................. 606/278 |
| 8,317,837 B2* | 11/2012 | Rezach et al. ................. 606/267 |
| 2002/0045899 A1 | 4/2002 | Errico et al. |
| 2002/0143332 A1 | 10/2002 | Lin et al. |
| 2002/0143341 A1 | 10/2002 | Biedermann et al. |
| 2002/0169450 A1 | 11/2002 | Lange |
| 2002/0183748 A1 | 12/2002 | Martin et al. |
| 2003/0000350 A1 | 1/2003 | Zhao et al. |
| 2003/0023240 A1 | 1/2003 | Amrein et al. |
| 2003/0045878 A1 | 3/2003 | Petit et al. |
| 2003/0055426 A1 | 3/2003 | Carbone et al. |
| 2003/0105460 A1 | 6/2003 | Crandall et al. |
| 2003/0149431 A1 | 8/2003 | Varieur |
| 2003/0149432 A1 | 8/2003 | Frigg et al. |
| 2003/0171751 A1 | 9/2003 | Ritland |
| 2003/0176864 A1 | 9/2003 | Ueyama et al. |
| 2003/0191473 A1 | 10/2003 | Taylor |
| 2003/0208202 A1 | 11/2003 | Falahee |
| 2004/0010253 A1 | 1/2004 | Morrison |
| 2004/0039383 A1 | 2/2004 | Jackson |
| 2004/0092930 A1 | 5/2004 | Petit et al. |
| 2004/0102780 A1 | 5/2004 | West |
| 2004/0147928 A1 | 7/2004 | Landry et al. |
| 2004/0158247 A1 | 8/2004 | Sitiso et al. |
| 2004/0215190 A1 | 10/2004 | Nguyen et al. |
| 2004/0243139 A1 | 12/2004 | Lewis et al. |
| 2004/0254574 A1 | 12/2004 | Morrison et al. |
| 2005/0070901 A1 | 3/2005 | David |
| 2005/0113830 A1 | 5/2005 | Rezach et al. |
| 2005/0113833 A1 | 5/2005 | Davison |
| 2005/0203516 A1 | 9/2005 | Biedermann et al. |
| 2005/0277923 A1 | 12/2005 | Sweeney |
| 2006/0079903 A1 | 4/2006 | Wong |
| 2006/0089647 A1 | 4/2006 | Culbert et al. |
| 2006/0149234 A1 | 7/2006 | De Coninck |
| 2006/0149245 A1 | 7/2006 | Sweeney |
| 2006/0195096 A1 | 8/2006 | Lee et al. |
| 2006/0241599 A1 | 10/2006 | Konieczynski et al. |
| 2007/0055239 A1 | 3/2007 | Sweeney et al. |
| 2007/0118122 A1 | 5/2007 | Butler et al. |
| 2007/0161996 A1 | 7/2007 | Biedermann et al. |
| 2007/0173833 A1 | 7/2007 | Butler et al. |
| 2008/0024173 A1 | 1/2008 | Nagai et al. |
| 2009/0043339 A1 | 2/2009 | Tepper et al. |
| 2009/0062860 A1 | 3/2009 | Frasier et al. |
| 2009/0093848 A1 | 4/2009 | Neary et al. |
| 2009/0099604 A1 | 4/2009 | Cho et al. |
| 2009/0131985 A1 | 5/2009 | Mazda et al. |
| 2009/0234391 A1 | 9/2009 | Butler et al. |
| 2009/0287253 A1 | 11/2009 | Felix et al. |
| 2010/0160971 A1 | 6/2010 | Glerum et al. |
| 2010/0198260 A1* | 8/2010 | Gabelberger et al. ......... 606/264 |
| 2010/0268279 A1 | 10/2010 | Gabelberger et al. |
| 2011/0004251 A1 | 1/2011 | Sweeney et al. |
| 2011/0172713 A1* | 7/2011 | Harper .......................... 606/264 |
| 2012/0029571 A1* | 2/2012 | Schwab et al. ................ 606/278 |
| 2012/0130426 A1 | 5/2012 | Thompson |
| 2012/0179204 A1 | 7/2012 | Rathbun et al. |

(56) References Cited

U.S. PATENT DOCUMENTS

FOREIGN PATENT DOCUMENTS

| WO | WO-2005/122965 | 12/2005 |
|---|---|---|
| WO | WO-2007/019204 | 2/2007 |

OTHER PUBLICATIONS

Chen, Pei-Yu et al., "Closed Reduction With Intramedullary Fixation for Midclavicular Fractures," Orthopedics journal, May 2004, pp. 459-462, vol. 27, No. 5.

European Patent Office Communication pursuant to Article 93(3) EPC for Application No. 05 757 401.4, date of mailing, Nov. 5, 2009 (6 pgs.).

International Search Report and Written Opinion for Application No. PCT/US05/20157, date of mailing Jan. 6, 2006, 8 pages.

Lamendola, Mark, "How to Use Belleville Washers Correctly," Dec. 1, 1997, EC&M, 2 pages.

Written Opinion for International Application No. PCT/US2006/030187, date of completion Jun. 20, 2007, 6 pages.

European Patent Office Communication pursuant to Article 93(3) EPC for Application No. 05 757 401.4, date of mailing, Nov. 5, 2009, 6 pages.

\* cited by examiner

SPINAL ROD CONNECTOR ASSEMBLY

CROSS REFERENCE TO RELATED APPLICATIONS

This patent application claims the benefit of and/or priority under 35 U.S.C. §119(e) to U.S. Provisional Patent Application Ser. No. 61/506,373 filed Jul. 11, 2011, entitled "Spinal Rod Connector Assembly" the entire contents of which is specifically incorporated herein by reference.

BACKGROUND OF THE INVENTION

Field of the Invention

The present invention relates to spine fixation components, constructs and assemblies and, more particularly, to spinal rod connector assemblies.

BACKGROUND INFORMATION

Spinal orthopedic assemblies and constructs such as spine plates, spinal bone screw assemblies for spinal rods as well as other spinal devices and/or components (collectively, spinal devices) have made a profound contribution to the correction of spinal deformities, accidents and other problems in the cervical, thoracic, lumbar and sacral spine. These and other spinal devices are typically fixed to vertebrae of the spine using vertebral bone screws. Vertebral bone screws are specially designed and manufactured bone screws that are placed into the bone of a vertebra. One typical placement of a bone screw for the fixation of a spinal component is through a pedicle of a vertebra. Vertebral bone screws placed in this manner offer superior strength and pull-out resistance as compared to other forms of spine fixation surgery. The ability to achieve pedicle fixation has allowed surgeons to obtain more secure fixation of the involved vertebral segments, which permits more powerful correction of spine problems and reported better clinical outcomes. Vertebral bone screws for pedicle fixation may be known as pedicle screws.

In addition to other uses, pedicle screws provide a solid foundation for the attachment of spinal rods. Spinal rods are used for the fixation of a plurality of vertebrae for various situations. A spinal rod is held relative to a pedicle screw by a spinal rod connector assembly attached to the pedicle screw. Various types of spinal rod connector assemblies are known such as those that allow for inter-operative adjustments in the coronal, transverse and sagittal planes. Certain spinal rod connector assemblies allow for various degrees of freedom for attachment to a pedicle screw from any direction, angle, and height. In all cases, however, the spinal rod connector assemblies hold a spinal rod and are fixed relative to the pedicle screw. Typically the spinal rod connector assembly is fixed relative to the pedicle screw through attachment of the spinal rod connector assembly to the pedicle screw head. Since a pedicle screw head may be cylindrical, spherical or ellipsoidal, the spinal rod connector assembly must be designed for the particular style of bone screw head.

Some spinal rod connector assemblies are configured so as to be positionable in a plurality of orientations relative to the vertebral bone screw prior to fixation. Once the spinal rod connector assembly is oriented relative to the vertebral bone screw head as desired, it is fixed against movement on and relative to the vertebral bone screw. The spinal rod connector assembly, however, must also provide a manner for fixing the spinal rod to the spinal rod connector assembly.

Fixation of the spinal rod to the spinal rod connector assembly may be accomplished in concert with the fixation of the orientation of the spinal rod connector assembly relative to and on the vertebral bone screw. In these types of spinal rod connector assemblies, torque applied to a spinal rod connector assembly component causes further spinal rod connector assembly components to fix orientation of the spinal rod connector assembly relative to and on the vertebral bone screw while affixing the spinal rod to the spinal rod connector assembly.

In this manner, spinal rods can be rigidly locked into a variety of positions along with other types of implant components. This allows a surgeon to tailor-make each construct for the individual case. In addition, some spinal rod connector assemblies are designed to provide for no in-situ threading. This decreases operative time by allowing the spinal rod connector assembly to be pre-assembled while the surgeon places the pedicle screws.

Even with the flexibility offered by the various prior articulating spinal rod connector assemblies, there is room for improvement. This is true particularly with respect to spinal rod connector assemblies that provide in concert fixing of orientation relative to and on a vertebral bone screw and the fixed retention of a spinal rod.

SUMMARY OF THE INVENTION

A spinal rod connector assembly for use/receipt on a vertebral bone screw has an articulating clamp for 1) fixing an orientation of the spinal rod connector assembly relative to and on the vertebral bone screw, and 2) attaching a separate spinal rod onto the spinal rod connector assembly in concert with one another.

The articulating clamp resides in a body of the spinal rod connector assembly and transfers a received downward force (torque) laterally to a spinal rod component of the spinal rod connector assembly which is configured to abut the spinal rod and hold the spinal rod between itself and a spinal rod holder of the spinal rod connector assembly. The articulating clamp thus improves the force transfer efficacy of the system.

The articulating clamp is defined by a front clamp portion and a rear clamp portion. The front and rear clamp portions each have two pivot notches that cooperate to define two pivot holes. Pivot pins interface with the two pivot holes in order to allow the clamp to articulate within a cavity in the body of the spinal rod connector assembly.

The front and rear clamp portions each have a clasping area configured to abut a cylindrical-headed vertebral bone screw. Together, the clasping areas of the front and rear clamps grasp the vertebral bone screw head upon application of torque. A chamfer is provided on upper ends of the front and rear clamp portions for interfacing with a chamfer of a torque screw or nut. Additionally, the front clamp portion has an enlarged or thickened upper end or lip that abuts the spinal rod component. The thickened upper lip applies an increase in lateral force against the spinal rod component during assembly lock-up compared to prior articulating systems.

The spinal rod component of the present spinal rod connector assembly provides improved overall gripping of the spinal rod by the system. This is achieved by incorporating an enlarged spinal rod interface area. A flange is also provided on the spinal rod component that increases the area of contact with the front clamp portion. The flange also acts as a stop to prevent the front clamp portion from advancing too far and over-angulating about the pivot point in order to ensure that both clamp portions are adequately retained within the body of the spinal rod connector assembly.

The present spinal rod connector assembly provides an improved ability to grip a spinal rod while maintaining safety and efficacy relative to current designs.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the figures.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN
EMBODIMENT OF THE INVENTION

Figure 1:
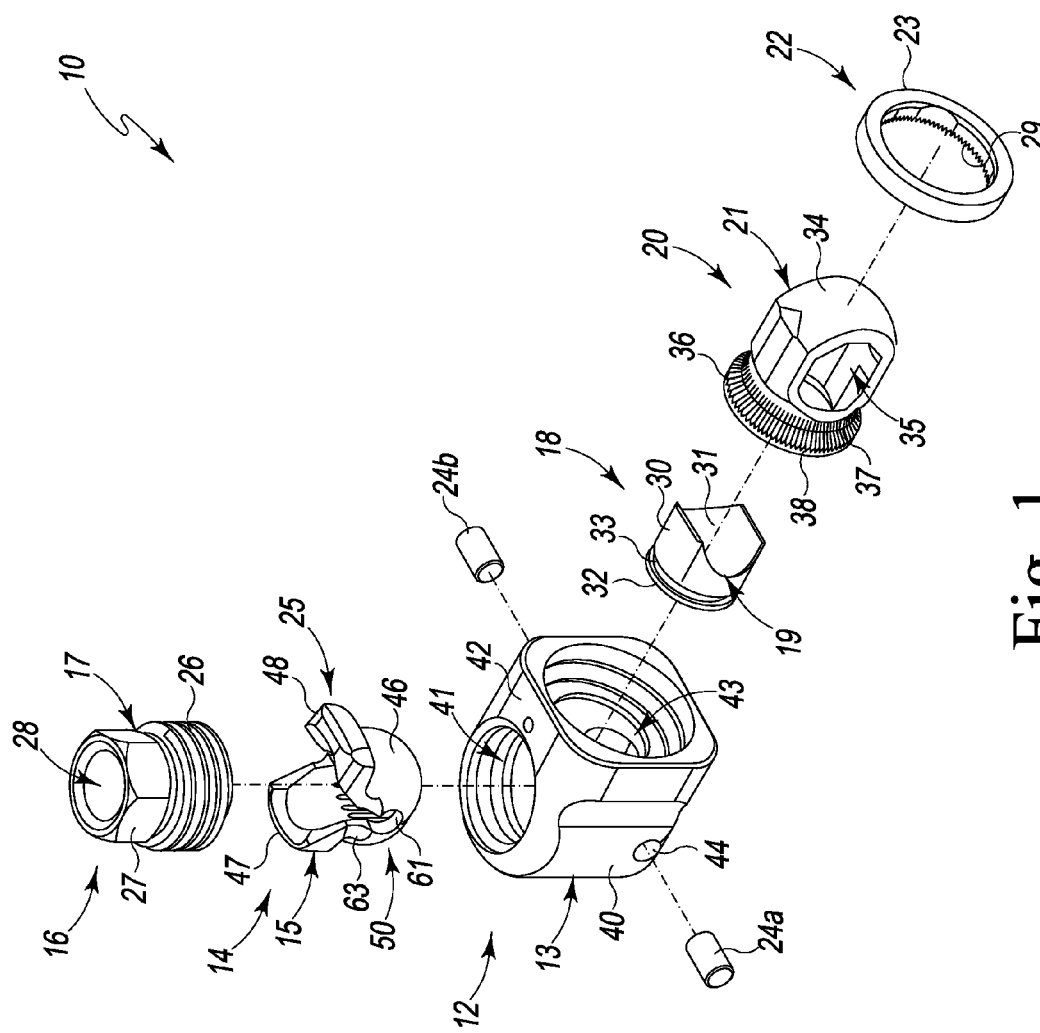
FIG. 1 is an exploded isometric view of a spinal rod connector assembly fashioned in accordance with the present principles.
Figure 2:
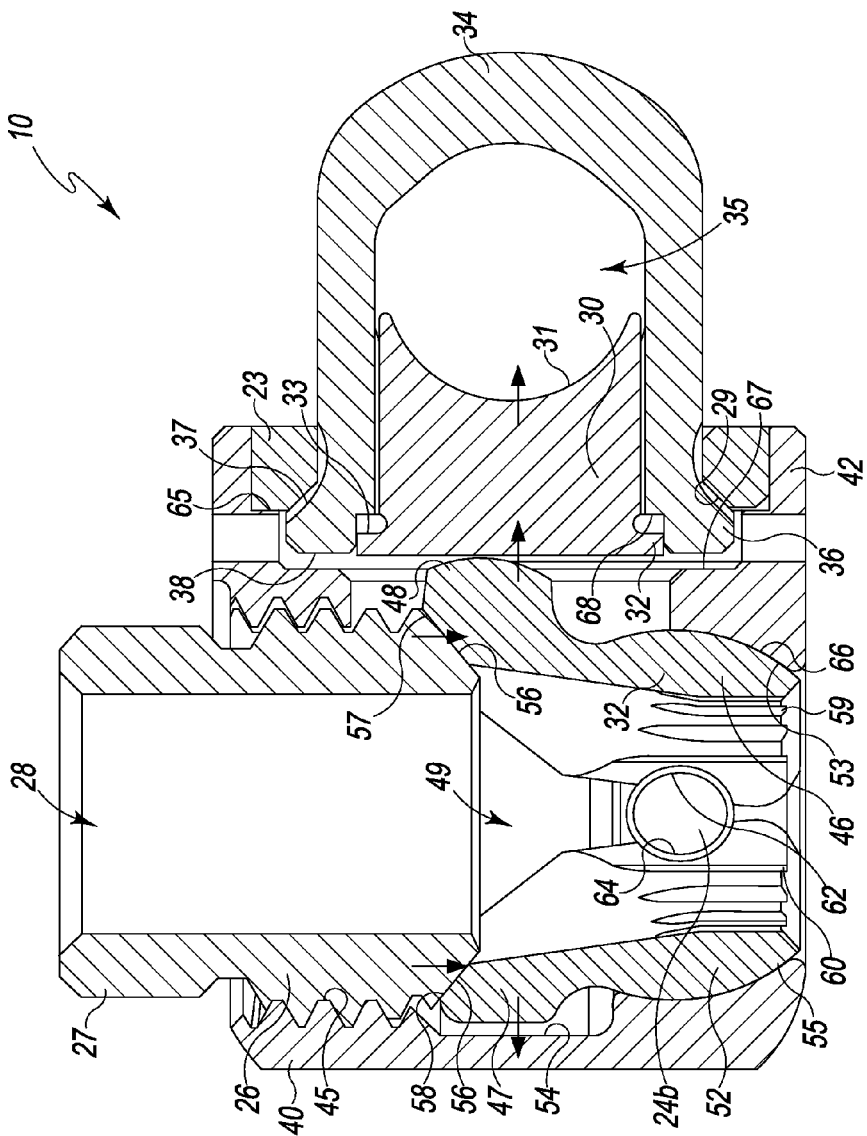
FIG. 2 is side sectional view of the spinal rod connector assembly of FIG. 1 in an assembled state.

Referring to FIGS. 1 and 2, there is depicted a spinal rod connector assembly, generally designated 10, fashioned in accordance with the present principles. The spinal rod connector assembly 10 includes a head 12, a clamp 14, a drive nut 16, a spinal rod cup 18, a spinal rod holder 20 and a weld ring 22. The spinal rod connector assembly 10 is configured and/or adapted to be retained on the head of a vertebral bone screw (not shown) and to retain a spinal rod (not shown) relative to the bone screw. The spinal rod connector assembly 10 is configured such that the assembly 10 is able to rotate about the vertebral bone screw head and be fixed in position relative thereto. Thus, the spinal rod connector assembly 10 may be positioned then fixed in various angular positions or orientations on the vertebral bone screw/bone screw head. Since a spinal rod (not shown) is fixedly retained by the spinal rod connector assembly 10, orientation of a spinal rod relative to the vertebral bone screw and vertebra is variable.

The head 12 is defined by a body 13 having a generally arced end/boss 40 and a generally rectangular front 42. The boss 40 has a bore 41 that extends from an upper end to a lower end thereof and defines an interior, cavity or space 49. The wall of the upper end of the bore 41 of the boss 40 includes threads/threading 45 therein that extend an axial distance downwardly into the bore 41. The wall of the lower end of the bore 41 of the boss 40 has an angle 53 that cooperates with the clamp 14 as described below to allow the clamp 14 to pivot or articulate within the space 49.

The front 42 has a bore 43 that extends from a side of the front 42 and into the space 49 such that the bores 41, 43 are in communication with one another, the bores 41, 43 being essentially transverse relative to one another. As best seen in FIG. 2, the bore 43 has a first circumferential inset, shelf or the like 65 at a first depth relative to the opening of the bore 43 and a second inset, shelf or the like 67 at a second depth relative to the opening of the bore 43 and to the first inset 65. These acts as stops as described below.

The body 26 further includes a first pivot bore 44 that extends from a first side of the boss 40 and into the bore 41, and a second pivot bore (not seen) that extends from a second side of the boss 40 and into the bore 41. The first and second pivot bores 44 are axially aligned such that first and second pivot pins 24a, 24b may extend through the first and second pivot bores 44 and through the space 49. The pivot pins 24a, 24b are held within the pivot bores 44 and provide a pivot point for the clamp 14 within the body 13. The pivot pins 24a, 24b are centered about the internal spherical diameter of the body 13.

The clamp 14 is received in the head 12 with the pivot pins 24a, 24b extending therethrough. The clamp 14 may also be termed a pivot clamp since the clamp 14 rotates or pivots about an axis defined by the pivot pins 24a, 24b. The pivot pins 24a, 24b thus control the pivot positions of the clamp 14. The clamp 14 is defined by a front clamp portion 25 and a rear clamp portion 15. The front clamp portion 25 has a lower end 46 having a spherical outer surface 66 and a spherical inner surface 59 with vertical grooves therein to form teeth. The rear clamp portion 15 has a lower end 52 having a spherical outer surface 55 and a spherical inner surface 60 with vertical grooves therein to form teeth. The radii of the spherical lower ends 46, 52 correspond to the curvature of the lower wall 53 of the bore 41 in order to allow the front and rear clamp portions together as the clamp 14 to freely articulate within the body 13.

The front clamp portion 25 has a first hemispherical cutout 61 (see FIG. 1) on a first lateral side thereof, and a second hemispherical cutout 62 (see FIG. 2) on a second lateral side thereof. Likewise, the rear clamp portion 25 has a first hemispherical cutout 63 (see FIG. 1) on a first lateral side thereof, and a second hemispherical cutout 64 (see FIG. 2) on a second lateral side thereof. Opposite hemispherical cutouts of the front and rear clamp portions 25, 15 form pivot pin holes one of which (clamp pivot pin hole 50 formed by hemispherical cutouts 61, 63) is seen in FIG. 1. The hemispherical cutouts 62, 64 as seen in FIG. 2 form the other clamp pivot pin hole. The hemispherical cutouts 61, 62, 63, 64 are sized to provide a hole diameter sufficient to accommodate the pivot pins 24a, 24b.

The upper end 48 of the front clamp portion 25 defines a thickened lip. The thickened upper lip 48 transmits the torque applied from the drive nut 16 into a lateral force onto the spinal rod cup 18. The upper end 47 of the rear clamp portion 15 defines a lip that is thinner than the lip of the front clamp portion 25. The thinner lip of the rear clamp portion 15 ensures that the rear clamp portion 15 has adequate room to articulate within the body 13. The front and rear clamp portions 25, 15 are thus asymmetrical. The front and rear clamp portions 25, 15, during articulation, work in concert to grab onto the bone screw head or post with the assist of the teeth of the inner walls 59, 60 thereof. The toothed inner walls 59, 60 increase the surface area of contact with the screw post and thus provide an enhanced grip onto the screw post.

The drive nut or screw 16 is defined by a generally cylindrical body 17 having an upper hex head portion 27 and a lower outwardly threaded portion 26. A bore 28 extends through the body 17 from a top or upper side of the hex head 27 to the threaded end 26. The threaded end 26 is sized to be threadedly received in the threads 45 of the bore 41 of the body 13. The hex head 27 is thus configured to receive a hex driver/tool (not shown) in order to thread the drive nut 16 into the head 12.

The drive nut 16 includes a chamfer 56 on the lower end of the threaded portion 26. The chamfer 56 interfaces and abuts the chamfer 57 of the upper end 48 of the front clamp portion 25 and the chamfer 58 of the upper end 47 of the rear clamp portion 15. As the drive nut 16 is threaded into the bore 41, the chamfer 56 of the drive nut 16 engages the chamfer 56 of the upper end 48 of the front clamp portion 25, and the chamfer 58 of the upper end 47 of the rear clamp portion 15. The force (torque) applied by the nut 16 (represented by the two down arrows at the bottom of the nut in FIG. 2) makes the front and rear clamp portions 25, 15 spread out within the cavity 49. This causes the lower ends 46, 52 of the front and rear clamp portions 25, 15 to draw together about the screw post. The lip 47 moves laterally (as represented by the arrow on lip 47 in FIG. 2) against the wall 54 of the space 49 in order to stop its movement. Additionally, the lip 48 of front clamp portion 25 moves against the spinal rod cup 18 which in turn laterally moves (as represented by the lateral arrows on the spinal rod cup 18) against a spinal rod (not shown) within the spinal rod hole 35 of the spinal rod holder 20. This restrains the spinal rod from movement relative to the spinal rod holder 20.

The rod holder 20 has a generally bullet-shaped body 21 having a nose portion 34 at a first end thereof and an annular portion 36 at a second end thereof. The nose portion 34 defines a hole 35 for receiving a spinal rod (i.e. spinal rod hole 35). The inner surface of the hole 35 is curved in like manner as the curvature of a spinal rod in order to snugly accommodate a side of the spinal rod. The annular outer surface 37 of the annular end 36 has a plurality of teeth. The annular inner surface 38 of the annular end 36 is generally smooth. An annular ledge 68 is formed in the bore of the annular end which serves as a stop for the spinal rod cup 18.

The weld ring 22 is defined by an annular body 23 that is of a diameter in order to fit into the bore 43 of the body, but be stopped or captured by the first ledge 64 of the bore. The rear annular surface 29 of the body 23 has a chamfer on its lower end. The chamfered surface 29 has teeth about its circumference that mesh with the outer surface teeth 37 of the rod holder 20. Thus, as the spinal rod cup 18 is moved into the spinal rod holder 20, the spinal rod holder 20 is moved against the weld ring 22. The outer surface teeth 37 of the rod holder 20 engage the chamfered surface teeth 29 of the weld ring 22 to prevent the rod holder 20 from rotating upon final lock down.

The spinal rod cup 18 is defined by a body 19 having a cylindrical portion 30 and a rear circumferential flange 32. The cylindrical portion 30 has a radial face 31 that interfaces with the spinal rod. The radial cut of the face 31 is slightly undersized with respect to the spinal rod it interfaces with, in order optimally grip onto the spinal rod and ensure enhanced lock down of the spinal rod. Applicant has observed that a radial cut of a consistent 2.70 mm radius increases the surface area of contact with the spinal rod to improve overall spinal rod gripping capabilities of the assembly 10.

The rear flange 32 has a large circumferential rear face (see FIG. 2) in order to provide a large surface area of contact for the upper end lip 48 of the front clamp portion 25. This allows for a more efficient transmission of force. The flange 32 also acts as a stop to prevent the spinal rod cup 18 from traveling too far within the rod holder 20, causing over articulation of the front clamp portion 25 (over angulating about the pivot point to ensure both pivot clamp portions are adequately retained in the head 12. Particularly, an undercut 33 in the front annular surface of the flange 32 provides the stop surface that abuts the annular ledge 68 of the rod holder 20. The spinal rod cup 18 is thus designed to receive the force from the clamp and then move against a spinal rod in the spinal rod holder.

The various components of the present spinal rod connector assembly 10 are made from a bio-compatible material such as stainless steel or titanium. Other bio-compatible materials, or course, may be used.

The present spinal rod connector assembly 10 is typically pre-assembled prior to when the surgeon receives the assembly. The surgeon will insert the spinal rod through the appropriate number of rod connector assemblies outside of the body and then use guides on the vertebral (pedicle) bone screws to slide the construct down onto the head/shank of the pedicle screw. Once the correct placement is achieved, the individual rod connector assemblies are tightened via the drive or locking nut or screw to lock down the assembly. As sufficient torque is applied to the drive nut the pivot clamps articulate to simultaneously lock down on the spinal rod and the bone screw head. Moreover, the teeth of rod holder and weld ring engage with one another to prevent the rod holder from rotating within the assembly to achieve final lock down. Lock down has been achieved with the assembly 10 through application of 100 in-lbs of torque applied to the nut.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spinal rod connector assembly for receipt on a vertebral bone screw, the spinal rod connector assembly comprising:
    a body defining an internal cavity, an upper opening in communication with the internal cavity, a lower opening in communication with the internal cavity, a lateral opening in communication with the internal cavity, and axially aligned first and second pivot bores in communication with the internal cavity;
    an articulating member situated in the internal cavity of the body, the articulating member defining first and second hemispherical cutouts, wherein the articulating member is configured to a) clamp onto a head of a vertebral bone screw received through the lower opening to fix orientation of the body relative to the head of the vertebral bone screw, and b) expand in a radial direction, both upon receipt of a downward force exerted on the articulating member;
    a first pivot pin received by the first pivot bore and the first hemispherical cutout;
    a second pivot pin received by the second pivot bore and the second hemispherical cutout;
    a spinal rod holder rotatably situated on the body at the lateral opening, the spinal rod holder configured to receive a spinal rod therethrough; and
    a spinal rod abutment member rotatably situated within the lateral opening of the body and extending into the spinal rod holder;
    wherein expansion of the articulating member in response to receipt of a downward force exerted on the articulating member moves the spinal rod abutment member into the spinal rod holder such that the spinal rod abutment surface abuts a spinal rod to fix the spinal rod to the spinal rod holder and fixes rotational orientation of the spinal rod holder.

2. The spinal rod connector assembly of claim 1, wherein the articulating member is pivotally retained in the internal cavity of the body via the first and second pivot pins.

3. The spinal rod connector assembly of claim 1, further comprising:

a retaining ring situated about the spinal rod holder adjacent the body, the retaining ring configured to aid in fixing the rotational orientation of the spinal rod holder in response to receipt of the downward force exerted on the articulating member.

4. The spinal rod connector assembly of claim 3, wherein:
the spinal rod holder includes a first set of teeth situated on an annular end of the spinal rod holder; and
the retaining ring includes a second set of teeth situated on an annular periphery of the retaining ring adjacent the first set of teeth;
wherein the first and second set of teeth mesh in response to receipt of the downward force exerted on the articulating member to thereby fix the rotational orientation of the spinal rod holder.

5. The spinal rod connector assembly of claim 1, wherein the articulating member includes an upper lip that abuts the spinal rod component in response to receipt of the downward force exerted on the articulating member.

6. The spinal rod connector assembly of claim 5, wherein the upper lip has a thickness that applies an increase in lateral force against the spinal rod component relative to the downward force exerted on the articulating member.

7. The spinal rod connector assembly of claim 1, wherein the articulating member has a clasping area at a lower end thereof that is configured to clamp onto the head of the vertebral bone screw.

8. The spinal rod connector assembly of claim 1, wherein the articulating member has a chamfer on an upper end thereof that is configured to interface with a chamfer of a torque nut.

9. The spinal rod connector assembly of claim 1, wherein;
the lower opening of the body is tapered; and
a lower end of the articulating member is tapered complementarily to the tapered lower opening of the body.

10. The spinal rod connector assembly of claim 1, wherein the articulating member pivots about an axis defined by the first and second pivot pins.

11. A spinal rod connector assembly for receipt on a vertebral bone screw, the spinal rod connector assembly comprising:
a generally rectangular body defining an internal cavity, an upper threaded bore in communication with the internal cavity, a lower bore in communication with the internal cavity, a lateral bore in communication with the internal cavity, and a first pivot bore in communication with the internal cavity;
an articulating member situated in the internal cavity of the body, the articulating member defining a first hemispherical cutout, wherein the articulating member is configured to a) clamp onto a head of a vertebral bone screw received through the lower bore to fix orientation of the body relative to the head of the vertebral bone screw, and b) expand in a radial direction, both upon receipt of a downward force exerted on the articulating member via a threaded nut received in the upper threaded bore;
a first pivot pin received by the first pivot bore and the first hemispherical cutout;
a spinal rod holder rotatably situated at the lateral bore, the spinal rod holder configured to receive a spinal rod therethrough; and
a spinal rod abutment member rotatably at least partially situated within the lateral bore of the body and extending into the spinal rod holder, the spinal rod abutment member having a first end in contact with a portion of the articulating member and a spinal rod abutment surface at a second end thereof that is within the spinal rod holder;
wherein expansion of the articulating member in response to receipt of a downward force exerted on the articulating member by the threaded nut moves the spinal rod abutment member into the spinal rod holder such that the spinal rod abutment surface abuts a spinal rod to fix the spinal rod to the spinal rod holder and fixes rotational orientation of the spinal rod holder.

12. The spinal rod connector assembly of claim 11, further comprising:
a retaining ring situated about the spinal rod holder adjacent the body, the retaining ring configured to aid in fixing the rotational orientation of the spinal rod holder in response to receipt of the downward force exerted on the articulating member by the threaded nut.

13. The spinal rod connector assembly of claim 12, wherein:
the spinal rod holder includes a first set of teeth situated on an annular end of the spinal rod holder that is received against a ledge of the lateral bore; and
the retaining ring includes a second set of teeth situated on an annular periphery of the retaining ring adjacent the first set of teeth;
wherein the first and second set of teeth mesh in response to receipt of the downward force exerted on the articulating member by the threaded nut to thereby fix the rotational orientation of the spinal rod holder.

14. The spinal rod connector assembly of claim 11, wherein the articulating member includes an upper lip that abuts the spinal rod component in response to receipt of the downward force exerted on the articulating member.

15. The spinal rod connector assembly of claim 14, wherein the upper lip has a thickness that applies an increase in lateral force against the spinal rod component relative to the downward force exerted on the articulating member.

16. The spinal rod connector assembly of claim 11, wherein the articulating member has a clasping area at a lower end thereof that is configured to clamp onto the head of the vertebral bone screw.

17. The spinal rod connector assembly of claim 11, wherein the articulating member has a chamfer on an upper end thereof that is configured to interface with a chamfer of the threaded nut.

18. The spinal rod connector assembly of claim 11, wherein;
the lower bore of the body is tapered; and
a lower end of the articulating member is tapered complementarily to the tapered lower bore of the body.

19. The spinal rod connector assembly of claim 11, wherein the body defines a second pivot bore in communication with the internal cavity, wherein the second pivot bore is axially aligned with the first pivot bore, and wherein the spinal rod connector assembly further includes a second pivot pin received by the second pivot bore and the second hemispherical cutout.

20. The spinal rod connector assembly of claim 19, wherein the articulating member pivots about an axis defined by the first and second pivot pins.

* * * * *